(12) United States Patent
Kumar (10) Patent No.: US 9,289,219 B2
(45) Date of Patent: Mar. 22, 2016

(54) DRILL BIT INCORPORATING DEPTH GAUGE

(76) Inventor: Pranesh Kumar, Rotorua (NZ)

( * ) Notice: Subject to any disclaimer, the term of this patent is extended or adjusted under 35 U.S.C. 154(b) by 648 days.

(21) Appl. No.: 13/521,916

(22) PCT Filed: Jan. 12, 2011

(86) PCT No.: PCT/NZ2011/000001
§ 371 (c)(1),
(2), (4) Date: Oct. 8, 2012

(87) PCT Pub. No.: WO2011/087379
PCT Pub. Date: Jul. 21, 2011

(65) Prior Publication Data
US 2013/0138106 A1  May 30, 2013

(30) Foreign Application Priority Data
Jan. 12, 2010 (NZ) ........................................ 574949

(51) Int. Cl.
*A61B 17/16* (2006.01)
*B23B 49/00* (2006.01)
*A61B 17/17* (2006.01)
*A61B 19/00* (2006.01)

(52) U.S. Cl.
CPC ......... *A61B 17/1637* (2013.01); *A61B 17/1617* (2013.01); *B23B 49/005* (2013.01); *A61B 17/17* (2013.01); *A61B 2019/462* (2013.01)

(58) Field of Classification Search
CPC ........... A61B 17/1615; A61B 17/1617; A61B 17/162; A61B 17/1633; A61B 17/7092; A61B 17/3494; A61B 5/150175; A61B 5/150198
USPC ................ 33/832, 833, 836; 408/202, 241 S; 606/80
See application file for complete search history.

(56) References Cited

U.S. PATENT DOCUMENTS

| | | | | |
|---|---|---|---|---|
| 5,571,133 | A * | 11/1996 | Yoon | 606/185 |
| 5,766,221 | A * | 6/1998 | Benderev et al. | 606/232 |
| 7,165,336 | B2 * | 1/2007 | Kim | 33/512 |

* cited by examiner

*Primary Examiner* — Anu Ramana
(74) *Attorney, Agent, or Firm* — Greer, Burns & Crain, Ltd.

(57) ABSTRACT

There is provided a drill bit for use in forming holes in a material, and measuring the depth of the hole. The drill bit includes a body providing a cutting region for making holes, a cannulation along the length of the cutting region, and an insert disposed within the cannulation. The insert is movable with respect to the body so as to selectively project beyond the cannulation, and edges of the cutting region.

17 Claims, 7 Drawing Sheets

DRILL BIT INCORPORATING DEPTH GAUGE

STATEMENT OF CORRESPONDING APPLICATIONS

This application is based on New Zealand Patent Application Number 574949, the entire contents of which are incorporated herein by reference.

BACKGROUND

The present invention relates to a drill, and in particular a surgical drill.

BACKGROUND ART

Screw application is one of the commonest procedures in orthopaedic surgery. A screw is inserted into a bone to secure a plate or reinforcing component in position. Drilling a hole is the obligatory first step of this procedure. In the normal procedure a hole is made with a specified diameter drill bit. A drill guide is used to protect the soft tissue and orient the direction of the hole. The drill is then removed, and the depth of the hole is measured using a third instrument called a depth gauge. However, it is difficult to accurately measure the hole depth. This may be due to several reasons including loosing the hole, missing the hole direction, or difficulty in engaging the end of the hole to accurately measure its depth.

There are a number of devices known to form holes in materials, and for use in surgical applications. A selection of this prior art is discussed below to provide context for the present invention.

U.S. Pat. No. 5,895,389 discloses a drill guide and measuring instrument. The device is configured such that hole depth is indicated as this is made.

A drill bit is driven by a rotary actuator. A telescoping plunger is provided so that forward movement of the drill bit is reflected on a gauge. A guide is used to orientate the drill bit adjacent to bone in which a hole is to be made.

However, the device of U.S. Pat. No. 5,895,389 suffers from the limitation that it's depth indication is dependent on the distance which the drill has penetrated. That distance does not necessarily correlate to the size of the hole made in the bone. That is, the drill bit may penetrate deeper (make a larger hole overall) than that formed in the bone. Accordingly, relying on the depth indication provided by the device of U.S. Pat. No. 5,895,389 provides unsatisfactory results.

U.S. Pat. No. 5,941,706 discloses a medical or dental drill. The drill bit has coloured bands disposed along its length. The bands provide an indication as to the depth of the hole formed using the drill bit. However, the measurements are insufficiently accurate for many medical applications.

In addition, it is difficult to obtain a depth reading corresponding to the depth of hole formed in the bone, as opposed to total depth of the hole. Accordingly, the device of U.S. Pat. No. 5,941,706 is less than satisfactory for all medical applications.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

SUMMARY

According to one aspect of the present invention, there is provided a drill bit, including
  a body to provide a cutting region for making holes,
  wherein the body is cannulated along a portion of its length into an opening in the cutting region,
  an insert in the cannulation,
  a pusher to move the insert along the length of the cannulation,
  wherein once the cutting region is used to make a hole having a distal end and a near end, the pusher may be used to cause the insert to project out of the opening in the cutting region to facilitate the insert engaging the distal end of the hole thereby allowing the depth of the hole to be measured.

According to another aspect of the present invention, there is provided a method of drilling and measuring a hole, the method including the steps of:
  (a) Providing a drill bit, including a cutting region for making holes in a material;
  (b) Positioning the drill bit adjacent to the material in which a hole is to be made;
  (c) Rotating the drill bit so as to cause the cutting region to make the hole;
  (d) Moving a pusher so as to cause an insert to move along the length of a cannulation in the drill bit;
  wherein, step (d) causes the insert to project out of the opening in the cutting region to facilitate the insert engaging the distal end of the hole thereby allowing the depth of the hole to be measured.

According to another aspect of the present invention, there is provided a drill incorporating a drill bit as substantially described above.

Preferably, the present invention relates to a surgical drill bit for use in orthopaedic surgery. In this embodiment a hole is made in the bone. Reference will be made herein as such. However, this should not be seen as limiting as the present invention can be used in other applications where it is necessary to drill a hole in a material, and measure the depth of the hole.

Throughout the present specification the following terms should be understood as meaning:
  distal edge of the hole—being the edge of the hole in bone furthest from a rotary drive powering the drill bit;
  proximal edge of the hole—being the edge of the hole closest to a rotary drive powering the drill bit; and
  depth of the hole—being the distance between the proximal edge and distal edge of the hole.

Note that the terms distal edge and proximal edge are defined by reference to the bone in which a hole is made. That is because in the preferred embodiment it is the size of the hole formed in bone that it is desirable to measure. However, that should not be seen as in any way limiting on the scope of the present invention.

Throughout the present specification reference to the term "drill bit" should be understood as meaning a component for making holes.

In the preferred embodiment, the drill bit is a standalone component configured to be secured to a rotary drive. Reference as such will be made herein.

In this embodiment, the drill bit provides a connector configured to engage with a complementary connector on the rotary drive. For instance, the connector may be an appropriate shaped portion of the body configured to enable it to be inserted inside the "chuck" of a hand-held electric drill. This is as should be understood by those skilled in the art.

Alternatively, the drill bit may be formed integrally into a rotary drive such as an electric drill.

In yet a further embodiment, the drill bit may be rotated manually. Accordingly, the foregoing should not be seen as limiting.

Throughout the present specification, reference to the term "cutting region" should be understood as meaning the part of the drill bit which makes holes.

The cutting region provides a plurality of cutting edges for making holes in bone. This is as should be known to those skilled in the art.

In the particularly preferred embodiment, the cutting edges are provided by spiral shaped channels which extend substantially along the length of the cutting region. This is as should be known to those skilled in the art.

However, it is also envisaged that the cutting edges can take other shapes and/or configurations. Therefore, the foregoing should not be seen as limiting on the scope of the present invention.

Throughout the present specification, reference to the term "insert" should be understood as meaning a component which can project beyond the width of the cutting region.

In a preferred embodiment, the insert has dimensions such that it can extend out of the cannulation in the drill bit through an opening in the cutting region, and beyond the cutting edges.

This may be achieved by the insert being configured such that it can be selectively moved with respect to the drill bit's body. This may involve sliding the insert through or along the cannulation.

Alternatively, the insert may be a telescoping body. Therefore, the insert may project out of the cannulation opening into the cutting region.

In use, the insert is configured to selectively engage the edge of a bone in which a hole is formed, when the insert projects beyond the cutting region. This may be achieved by the insert increasing the overall width of the drill bit. This provides at least one point with a width greater than the width of the hole made in the bone. This facilitates the drill bit accurately measuring the hole formed in the bone. This aspect of the present invention should become clearer from the following discussion.

It should be understood that the insert provides a locking mechanism to secure the drill bit with respect to the distal edge of a hole formed in the bone. This facilitates the provision of an accurate reference point from which to measure the depth of the hole.

Throughout the present specification, reference to the term "pusher" should be understood as meaning a component to cause an insert to project beyond the cutting region.

The pusher may be a lever, button, detent or other component capable of engagement by a person.

Accordingly, the forgoing should not be seen as limiting and alternatives are envisaged as being within the scope of the present invention.

In a particularly preferred embodiment, the present invention includes a gauge.

Throughout the present specification, reference to the term "gauge" should be understood as meaning a component, assembly of components, other mechanism, markings or scale, to measure the depth of a hole.

In a preferred embodiment, the gauge may be provided by markings along the length of the drill bit.

In a particularly preferred embodiment of the present invention, the markings start at the cannulation opening into the cutting region. In this embodiment, the cannulation opening acts as a reference point from which the depth of the hole may be measured.

According to another aspect of the present invention, there is provided a drill bit, including
a body that provides a cutting region for making holes,
a gauge to measure the depth of a hole formed in a material, wherein the hole has a distal end and a proximal end,
characterised in that the drill bit includes
a locking mechanism to secure the drill bit with respect to the material in which a hole is made, so as to provide a fixed reference point and thereby facilitate measuring the distance between the proximal end of the hole and distal end of the hole.

In a particularly preferred embodiment, the locking mechanism may be provided by an insert disposed within a cannulation of the drill bit as substantially described above.

However; this should not be seen as limiting and other embodiments are envisaged as within the scope of the present invention.

BRIEF DESCRIPTION OF THE DRAWINGS

Preferred embodiments of the invention will be described by way of example only and with reference to the drawings, in which.

DETAILED DESCRIPTION

A drill bit incorporating depth gauge, generally indicated as element (1), is provided in accordance with the present invention. The drill (1) includes a drill bit (1a), an insert (2), a sleeve (3) and a handle (4).

The drill bit (1a) is formed from a shaft indicated generally by (5). The shaft (5) is circular in cross section with a diameter in the range of 2.7 mm to 6.5 mm. Its length can range from 40 to 160 mm.

Externally, the drill bit (1a) can be made to have the same appearance of any standardised surgical drill.

End (6) of shaft (5) provides an attachment point to facilitate securing the drill bit (1a) to a rotary drive (not shown in the drawings). The end (6) is shaped to correspond to a "clip n lock" attachment system as should be known to those skilled in the art.

Shaft (5) provides a cutting region, which is indicated generally by line (7).

The cutting region (7) has 2-4 spiral shaped cutting edges (21) that extend along the length of the shaft (5). The cutting region's diameter is similar to that of shaft (5), while its length can vary from 40 mm to 60 mm depending on indented use of the drill bit (1a).

The shaft (5) end cutting region (7) have a cannulation (9) with a diameter of between 0.5 mm-1 mm. The cannulation (9) lies in mid axis to the diameter of the shaft and the cutting region.

Cannulation (9) has a first opening of drill bit (1a) and a notch (11). The opening (8) is towards drill bit end (12). Note the opening is near the tip of the cutting region (7) rather than at the tip itself.

The notch (11) is towards end (6) and is an opening into cannulation (9). The notch (11) is typically 3 mm in length and 1-1.5 mm in width.

The cannulation (9) accommodates the insert (2). That is, insert (2) is disposed in cannulation (9).

The insert (2) is typically 0.1 mm smaller in diameter than the cannulation (9). Insert end (13) is generally flush with opening (8). Insert end (14) passes through the notch (11) and is connected to a pusher (15).

A spring (not shown) can be attached to the insert (2). The spring urges the insert (2) towards a retracted position in which it is entirely inside the cannulation (9). When retracted inside the cannulation (9), insert end (13) is flush with opening (8).

Sleeve (3) has a far end (14a) and a near end (14b). A cannulation (16) in sleeve (3) has a diameter slightly larger than the width at the shaft (5). The cannulation (16) allows the shaft (5) to easily pass through the sleeve (3). The far end (14b) of the sleeve (3) is smooth to engage the screw hole of the plate. An indentation (17) is provided in sleeve (3) to allow engagement by handle (4).

Sleeve (3) can act to protect soft tissue around the bone where the hole is to be made. In addition, the sleeve (3) may also act as a drill guide and an aid in measuring the depth of a hole formed in bone.

The shaft (5) is marked with length markings (18). The markings (18) correspond to the distance from the opening (8), back along the length of shaft (5) and towards end (6). In use, the distance from the opening (8) is indicated by sleeve (3) which is slid along the length of the shaft, so that it abuts the proximal end of a hole. This facilitates the depth of the hole being measured. This should become clearer form the following discussion.

A handle (19) is provided. The handle (19), is a flat structure measuring about 1-2 cm×7 cm. End (20) of handle (19) is shaped to provide an engagement means. The engagement means engages indentation (17) in sleeve (3). This facilitates a person orientating and holding the drill bit (1a) when in use.

The handle (19) is smoothened to provide a good hand grip. It will be used to manipulate the sleeve (3), it provides control of the drill, and may help in achieving a desired direction for a hole.

Use of the drill bit (1a) will now be described.

Figure 1:
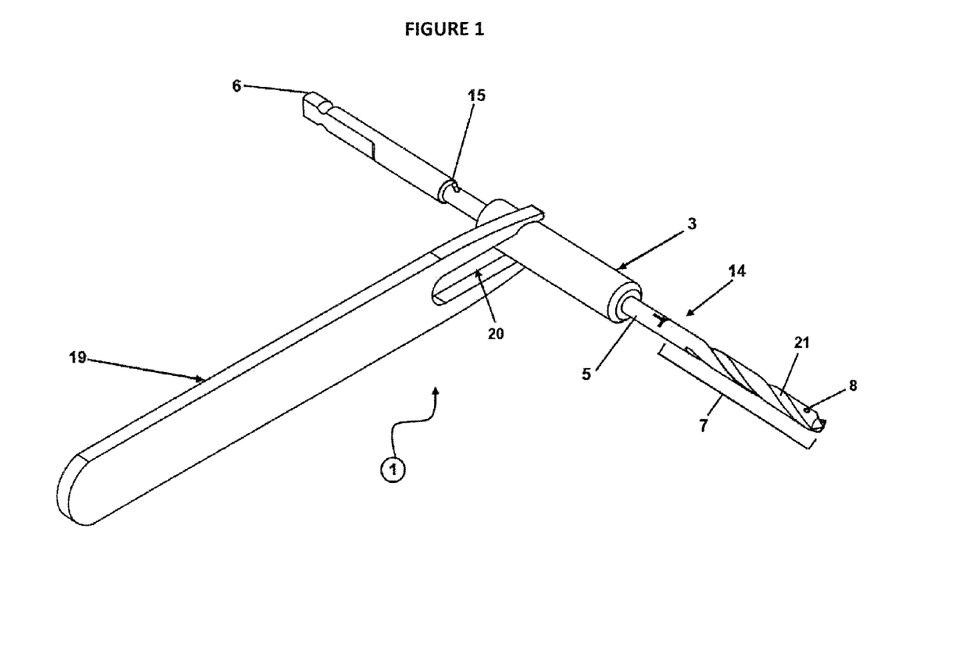
FIG. 1 shows an assembled Drill bit incorporating depth gauge according to the present invention.
Figure 2:
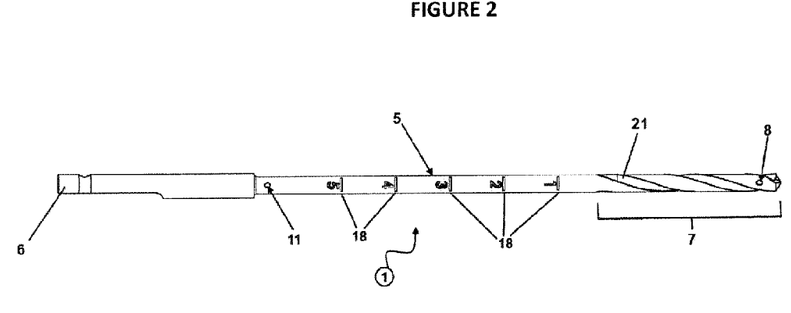
FIG. 2 shows a drill bit component of a Drill according to the present invention.
Figure 3:
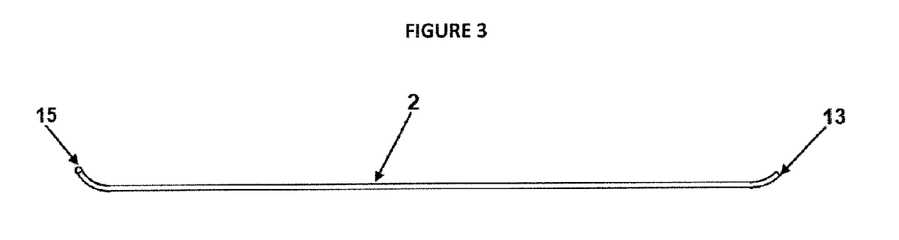
FIG. 3 shows an insert component of a Drill according to the present invention.
Figure 4:
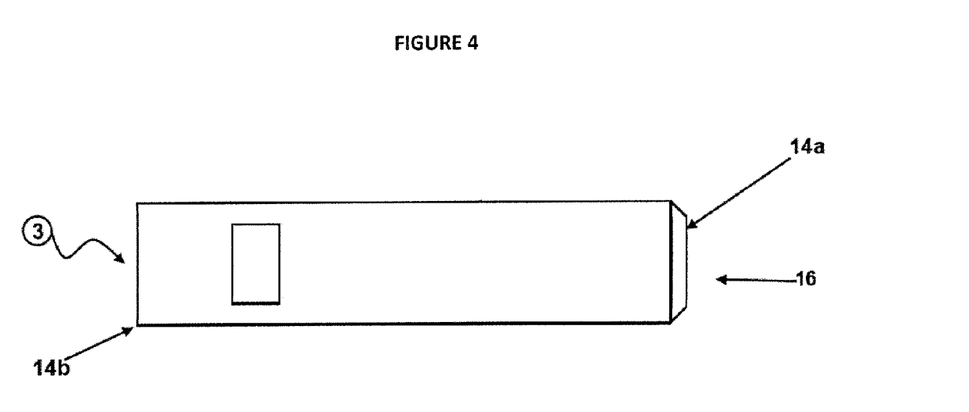
FIG. 4 shows a sleeve component of a Drill according to the present invention.
Figure 5:
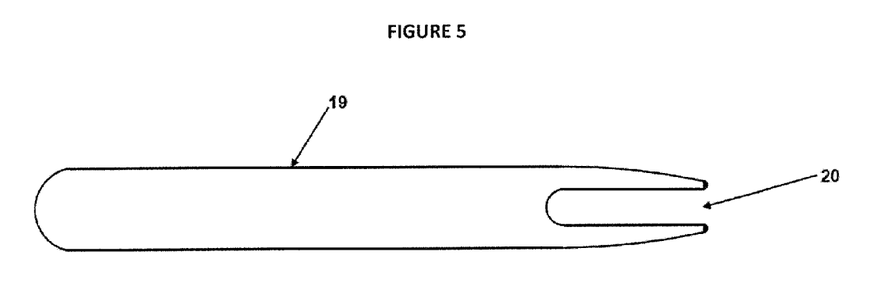
FIG. 5 shows a handle component of a Drill according to the present invention.
Figure 6:
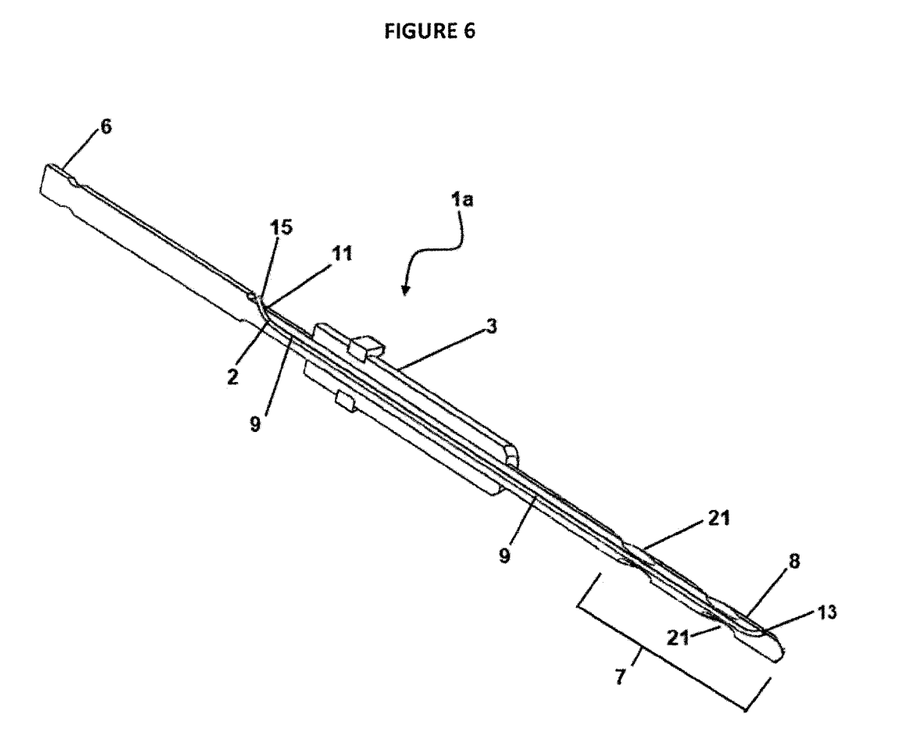
FIG. 6 shows a side perspective cross sectional view of a Drill according to the present invention.
Figure 7A:
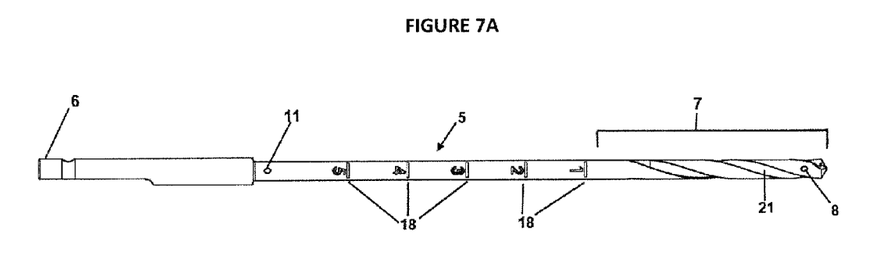
FIG. 7A shows a side cross sectional view of FIG. 2.
Figure 7B:
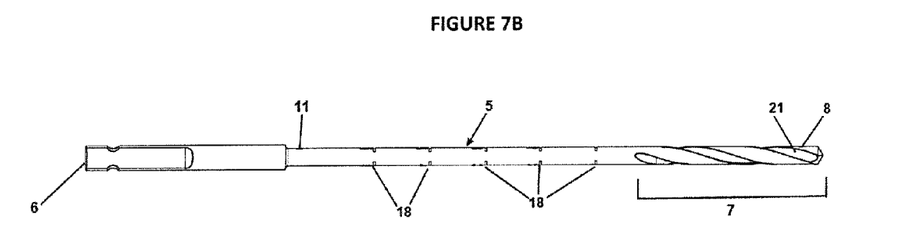
FIG. 7B shows an alternative side view of FIG. 7A.

The components of the drill bit (1a) are assembled into the form shown in FIG. 1. The attachment end (6) is connected to a rotary drive of known type. Sleeve (3) is engaged by handle (19).

The handle (19) is used to position the drill bit (1a) against bone in which a hole is to be made. The handle also allows the user to orientate the drill bit (1a) to correspond to direction of the desired hole. Sleeve (3) is slid along the length of the shaft (5) so that end (14b) abuts soft tissue around the bone in which a hole is to be made. This allows sleeve (3) to protect the soft tissue and may prevent this being torn or ripped during making of the hole.

The rotary drive is engaged and causes the drill bit (1a) to rotate. The user applies pressure to the drill bit (1a), thereby causing the cutting edges (21) to form a hole in the bone. This continues until the user determines that a hole of sufficient size has been made.

The rotary drive is disengaged so that the drill bit (1a) stops rotating. The pusher (15) is engaged by the user. This causes insert end (13) to project out through opening (8). The user then pulls drill bit (1a) back, thereby causing the insert to abut the distal end of the hole. The sleeve (3) is then slid along the length of shaft (5) so that end (14b) touches or is close to the proximal end of the hole. The depth of the hole is read from length markings (10) on the shaft (5).

Once the depth is measured the pusher (12) is used to move insert (2) back into opening (8). That is, insert (2) is entirely within cannulation (9). The drill bit (1a) is then removed from the hole. A screw is chosen according to the length of hole measured using drill bit (1a). The screw is inserted into the hole according to techniques as should be known to those skilled in the art.

It will be appreciated that the dimensions and the proportions of the drill bit, insert, sleeve and handle may be varied as necessary to suit particular applications.

The drill of present invention can be made of any tough material suitable for surgical use. In one embodiment the drill bit shaft, and components may be made from surgical grade steel or other materials suitable for use in surgery. Alternatively, the shaft and components may be made from titanium oxide, or powder coated with titanium oxide.

It is preferred that the drill is cleaned after every application. It should be regularly washed and oiled after an operation.

It can be used for multiple procedures.

It can be sterilised using standard surgical sterilisation technique.

Aspects of the present invention have been described by way of example only and it should be appreciated that modifications and additions may be made thereto without departing from the scope thereof as defined in the appended claims.

What is claimed is:

1. A drill bit, including
   a body to provide a cutting region for making holes, wherein in use, the cutting region makes a hole having an edge that defines a distal end of the hole and an edge that defines a proximal end of the hole,
   wherein the body includes a cannulation in the cutting region and an opening in the cutting region which is in communication with the cannulation;
   wherein the drill bit includes an insert in the cannulation,
   a pusher to move the insert along the length of the cannulation to cause the insert to project out of the opening in the cutting region, and
   a gauge,
   wherein once the cutting region is used to make the hole, the pusher may be used to move the insert to project out of the opening in the cutting region to facilitate the insert engaging the edge of the hole which defines the distal end of the hole, thereby providing a fixed reference point from which the gauge measures a distance between the distal end and the proximal end of the hole.

2. The drill bit as claimed in claim 1, wherein the body provides an attachment end to connect to a rotary drive.

3. The drill bit as claimed in claim 1, wherein the gauge includes markings which indicate the distance between the distal end and the proximal end of the hole.

4. The drill bit as claimed in claim 1, including a sleeve which surrounds at least a portion of the body and is slidable with respect to the body, and wherein the sleeve, in use, is moved to abut or be near the proximal end of the hole to indicate the distance between the distal end and the proximal end of the hole.

5. The drill bit as claimed in claim 4, wherein the sleeve also acts as a guide.

6. The drill bit as claimed in claim 1, including a guide configured to orientate the drill bit to ensure correct direction of the hole.

7. The drill bit as claimed in claim 1, wherein the opening in the cutting region is near a tip of the drill bit.

8. The drill bit as claimed in claim 1, wherein the cutting region is configured to make a hole in bone.

9. The drill bit as claimed in claim 1, wherein the length of the cutting region is between 40 mm to 60 mm.

10. The drill bit as claimed in claim 1, including a spring to urge the insert towards a retracted position in which it is entirely inside the cannulation.

11. The drill bit as claimed in claim 1, including a handle to facilitate engagement and orientation of the drill bit in use.

12. The drill bit as claimed in claim 1, wherein the body is made from titanium oxide.

13. The drill bit as claimed in claim 1, wherein the body is made from surgical grade stainless steel.

14. The drill bit as claimed in claim 1, wherein the body is coated with titanium oxide.

15. A method of drilling and measuring a hole, the method including the steps of:
   (a) providing a drill bit including a cutting region for making holes in a material;
   (b) positioning the drill bit adjacent to the material in which a hole is to be made;
   (c) rotating the drill bit so as to cause the cutting region to make the hole having an edge that defines a distal end of the hole and an edge that defines a proximal end of the hole;
   (d) moving a pusher so as to cause an insert to move along the length of cannulation in the drill bit;
   wherein, step (d) causes the insert to project out of the opening in the cutting region to facilitate the insert engaging the edge that defines the distal end of the hole thereby allowing measurement of the distance between the distal end of the hole and the proximal end of the hole.

16. The drill bit as claimed in claim 15, wherein the cutting region has a plurality of cutting edges.

17. The drill bit as claimed in claim 16, wherein the cutting edges are provided by spiral shaped channels which extend along the length of the cutting region.

* * * * *